United States Patent [19]

Kojima et al.

[11] Patent Number: 4,629,549
[45] Date of Patent: Dec. 16, 1986

[54] OXYGEN SENSOR

[75] Inventors: Takao Kojima; Yutaka Nakayama; Hiroyuki Ishiguro; Tetsusyo Yamada, all of Nagoya, Japan

[73] Assignee: NGK Spark Plug Co., Ltd., Nagoya, Japan

[21] Appl. No.: 751,269

[22] Filed: Jul. 2, 1985

[30] Foreign Application Priority Data

Jul. 17, 1984 [JP] Japan ................. 59-148282

[51] Int. Cl.⁴ .......................................... G01N 27/58
[52] U.S. Cl. .................................... 204/406; 204/412; 204/425
[58] Field of Search ................ 204/406, 425, 412, 15, 204/426

[56] References Cited

U.S. PATENT DOCUMENTS

| | | | |
|---|---|---|---|
| 4,345,985 | 8/1982 | Tohda et al. | 204/426 X |
| 4,395,319 | 7/1983 | Torisu et al. | 204/426 |
| 4,462,890 | 7/1984 | Touda et al. | 204/425 |
| 4,505,806 | 3/1985 | Yamada | 204/425 |
| 4,505,807 | 3/1985 | Yamada | 204/425 |

Primary Examiner—G. L. Kaplan
Attorney, Agent, or Firm—Oblon, Fisher, Spivak, McClelland & Maier

[57] ABSTRACT

In an oxygen sensor which is provided with an oxygen pump element having electrodes on both front and rear surfaces of a solid electrolyte plate with oxygen ion conductive property, voltage from an external power source is applied between the electrodes and a pumping current flows between the electrodes. Thereby oxygen is pumped out of ambient gases to be measured through a member including a gap with oxygen diffusion limiting property. The limit value of the pumping current accompanied by the oxygen pumping is determined or the oxygen concentration difference produced before and after the diffusive motion of oxygen through the member or oxygen concentration produced after the diffusive motion of oxygen through the member is measured. Thereby the oxygen concentration of the ambient gases is calculated. The oxygen sensor comprises a heater unit installed on the solid electrolyte plate of the oxygen pump element through an electric insulation layer, and a lead wire unit of one electrode of the oxygen pump element connected at one end to the heater unit. Thus the oxygen sensor is excellent in energy saving, detection accuracy, and reduction of use amount of electrode lead wires.

10 Claims, 15 Drawing Figures

4,629,549

OXYGEN SENSOR

BACKGROUND OF THE INVENTION (1) Field of the Invention

The present invention relates to oxygen sensors and more specifically to a device for detecting the concentration of oxygen or a combustible constituent in gases utilizing an oxygen pump by means of a solid electrolyte body—i.e.) so-called oxygen sensor in a broad meaning.

(2) Description of the Prior Art

In the prior art, measurement of oxygen concentration in gases, particularly electric measurement, is performed by devices in which a cathode surface that is one electrode surface of a solid electrolyte oxygen pump element is sealed. A wall to seal the cathode surface is provided with fine diffusion holes (hereinafter referred to as "fine holes"), and oxygen in gases to be measured is introduced through the fine holes by means of diffusion phenomenon. At the same time the amount of current caused to flow by applying a prescribed voltage to both electrode surfaces is measured. The oxygen concentration in the gases is calculated from the measured current flow as disclosed in so-called diffusion limiting current measuring method (Japanese published unexamined patent application No. Sho 52-72286, Toyota Chuo Kenkyusho; Japanese published unexamined patent application No. Sho 53-66292, Westinghouse "Combustible Substance Sensor").

On the other hand, Japanese published unexamined patent application No. Sho 58-153155 proposes an oxygen sensor having an excellent response property where a narrow gap is formed in a pumping surface of an oxygen pump element, and an oxygen concentration cell element as an oxygen gas shielding body is arranged in opposition thereto. Limitation of the diffusion motion of the oxygen gas caused by the pumping of the oxygen pump element is effected by an open and edge portion of the narrow gap. In these oxygen sensors, however, since a pumping power source applied between the electrodes of the oxygen pump element and a heater power source to heat a sensor are separately installed, the device becomes complicated and expensive.

OBJECTS OF THE INVENTION

In order to eliminate above-mentioned disadvantages in the prior art, an object of the invention is to provide an oxygen sensor where a power source for a heater and an oxygen pump element is simplified and the cost for the power source can be reduced.

Another object of the invention is to provide an oxygen sensor where current control and temperature control can be effected accurately and simply.

Still another object of the invention is to provide an oxygen sensor where the use amount of lead wires for the heater or electrodes is reduced, thereby reducing the cost.

SUMMARY OF THE INVENTION

The subject-matter of the invention to attain above objects is as hereinafter described.

In an oxygen sensor which is provided with an oxygen pump element having electrodes on both front and rear surfaces of a solid electrolyte plate with oxygen ion conductive property, voltage from an external power source is applied between the electrodes and a pumping current flows between the electrodes. Oxygen is thereby pumped out of ambient gases to be measured through a member including a gap with oxygen diffusion limiting property. Limit values of the pumping current accompanied by the oxygen pumping are determined or oxygen concentration differences produced before and after the diffusive motion of oxygen through the member with diffusion limiting property by the oxygen pumping or the oxygen concentration produced after the diffusive motion of oxygen through the member are measured, and the oxygen concentration of the ambient gases is calculated. The oxygen sensor comprises a heater unit installed on the solid electrolyte plate of the oxygen pump element through an electric insulation layer. A lead wire unit of one electrode of the oxygen pump element is connected at one end to the heater unit.

DETAILED DESCRIPTION OF THE PRESENTLY PREFERRED EMBODIMENTS

Figure 1:
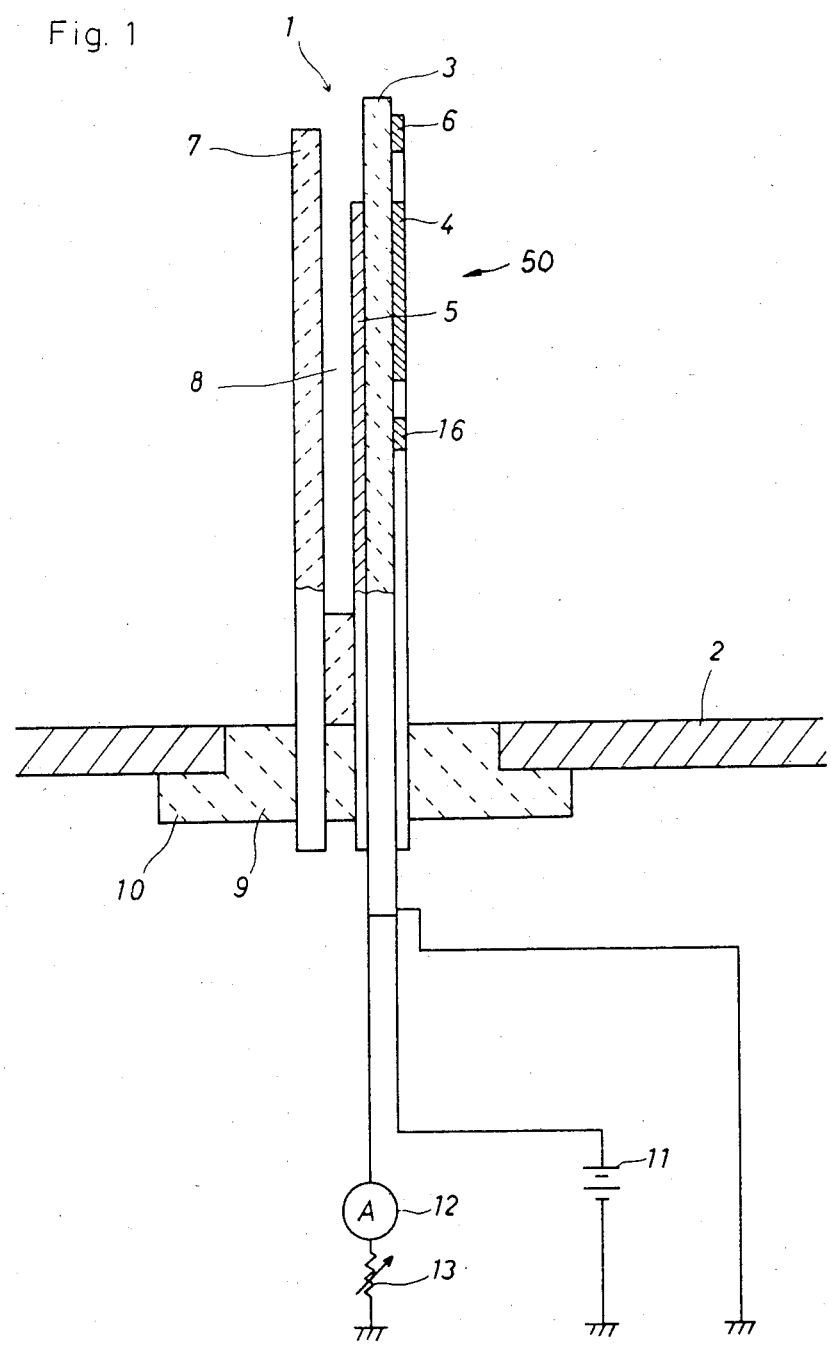
FIG. 1 is a longitudinal sectional view of a first embodiment of an oxygen sensor according to the invention arranged in an exhaust pipe of an internal combustion engine.
Figure 2:
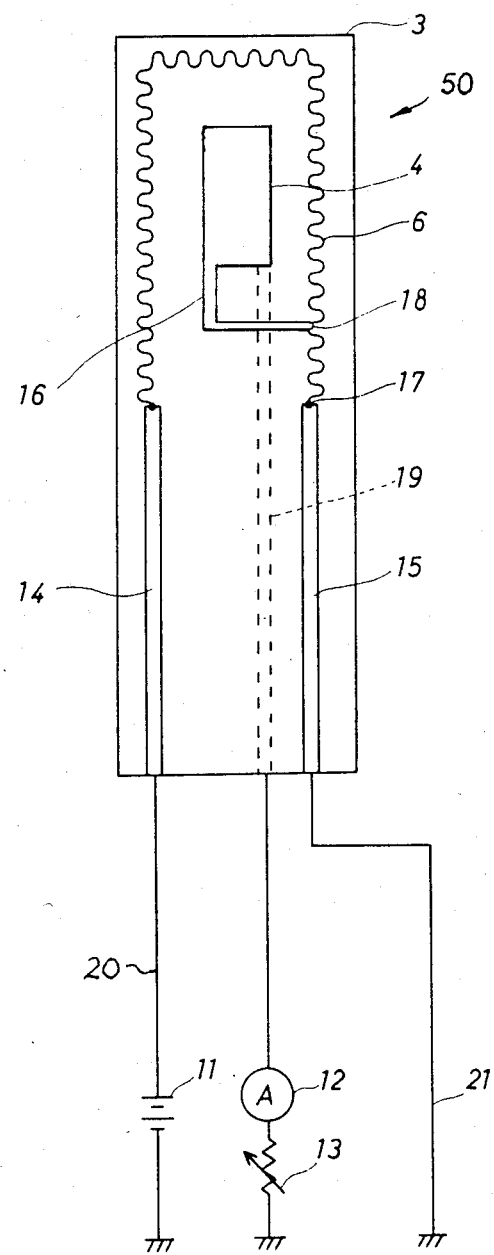
FIG. 2 is a plan view of the oxygen sensor in FIG. 1.

FIGS. 1 and 2 show a first embodiment of the present invention. FIG. 1 is a longitudinal sectional view of an oxygen sensor 1 of the embodiment applied to an exhaust pipe 2 of an internal combustion engine for automobiles, and FIG. 2 is a plan view of the oxygen sensor 1. A solid electrolyte plate 3 with oxygen ion conductive property is made of a solid electrolyte sintering body including zirconia as the main constituent. The solid electrolyte plate 3 is rectangular in form. Electrode layers 4, 5 with gas transmission property including platinum as the main constituent are printed on opposite surfaces of the solid electrolyte plate 3. The solid electrolyte plate 3 and the electrode layers 4, 5 constitute an oxygen pump element 50. A heater 6 of platinum or the like is formed on the outer circumference of the electrode layers 4, 5 using thick film technology.

A heat-resistant ceramic plate 7 functioning as an oxygen gas shielding body is parallel to and has nearly the same configuration as that of the solid electrolyte plate 3. A gap 8 of prescribed width separates the ceramic plate 7 from the solid electrolyte plate 3. Both the ceramic plate 7 and the solid electrolyte plate 3 are fixed to a bed 9 of disc form and further to the exhaust pipe 2 through a collar 10 of the bed 9.

Numeral 11 designates a battery to supply power to the solid electrolyte plate 3, the electrodes 4, 5 and the heater 6. Numeral 12 designates an ammeter to detect current flowing through the solid electrolyte plate 3 and the electrodes 4, 5. Numeral 13 designates a current amount control circuit such as a variable resistor.

FIG. 2 shows a plan view of the oxygen pump element 50 of the oxygen sensor 1. In FIG. 2, the heater 6 is formed to the side of the electrode 4 at the edge portion of the solid electrolyte plate 3 outside the electrode layer 4. The heater 6 meanders in U-like form, and the solid electrolyte plate 3 is heated from the outer edge portion by energizing the heater 6. The two ends of the heater 6 are connected respectively to lead wires 14, 15 for the heater 6. One end of a lead wire 16 for the electrode layer 4 is connected to the heater 6 at a junction 18 slightly higher than a junction 17 of the heater 6 with the lead wire 15. The electrode layer 5 on the rear side of the solid electrolyte plate 3 is connected to a lead wire 19. The lead wires 16, 19 are made of material similar to that of the electrode layers 4, 5—for example, platinum. The electrode layers 4, 5, the heater 6, and the lead wires 14, 15, 16, 19 are printed on the solid electrolyte plate 3 using thick film technology.

The lead wire 14 is connected to the positive electrode of the battery 11 by a wire 20, and the lead wire 15 is connected to a ground wire 21. The lead wire 19 is connected through the ammeter 12 to the variable resistor 13, and one end of the variable resistor 13 is grounded. Thus the electrode layers 4, 5 of the solid electrolyte plate 3, a part of the heater 6, and the lead wire 15 are connected in parallel to the battery 11.

Figure 3A:
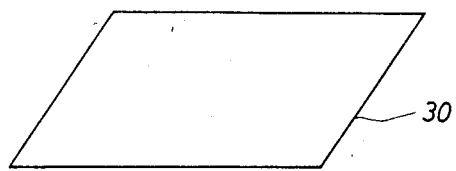
FIGS. 3a, b, c, d and e are diagrams, illustrating the manufacturing process of the oxygen sensor of the first embodiment.
Figure 3B:
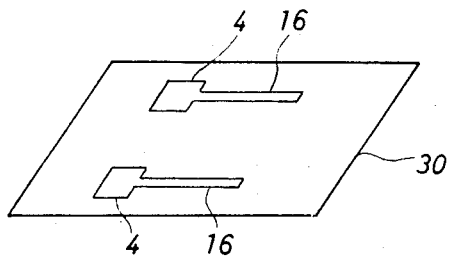
Figure 3C:
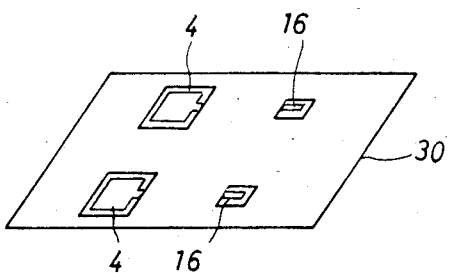
Figure 3D:
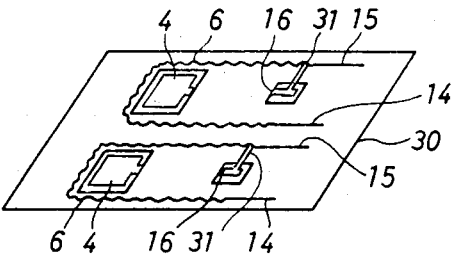
Figure 3E:
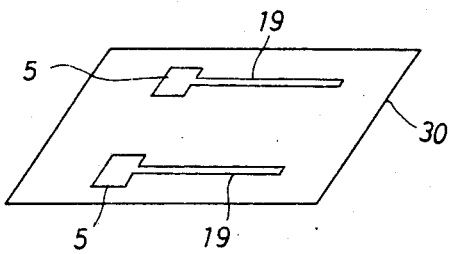

A method for manufacturing the oxygen pump element 50 will now be described. FIGS. 3(A), (B), (C), (D) and (E) show a process for manufacturing the oxygen sensor 1. FIG. 3(A) shows a solid electrolyte sheet 30 made of zirconia. FIG. 3(B) shows a process for printing the electrode layer 4 and the lead wire 16 onto a surface of the solid electrolyte sheet 30. FIG. 3(C) shows a process for printing an insulation cost as an electric insulation layer onto the same surface of the sheet 30. In this case, the electrode layer 4 and the end portion of the lead wire 16 remain without the insulation cost. FIG. 3(D) shows a process for printing the heater 6 and the lead wires 14, 15 onto the insulation coat. In this case, a lead wire 31 is further printed so as to connect the end portion of the lead wire 16 to the heater 6. FIG. 3(E) shows a process for printing the electrode layer 5 and the lead wire 19 onto the rear surface of the solid electrolyte sheet 30. And then the solid electrolyte sheet 30 is cut into a prescribed shape, the lead wires are drawn, and the oxygen sensor 1 is sintered.

The solid electrolyte to constitute the solid electrolyte plate 3 may be not only zirconia but also other materials having oxygen ion conductive property. For example, a solid solution of zirconia with yttrium or calcia or a solid solution of cerium dioxide, thorium dioxide, and hafnium oxide may be used.

The electrode layers 4, 5 formed on the surface of the solid electrolyte plate 3 may be made using powders of Pt, Ru, Pd, Rh, Ir, Au, Ag etc. as the main constituent. The powders are converted into a paste state, the paste is printed on a prescribed portion of the solid electrolyte plate using thick film technology, and then the powders are sintered into a heat-resistant metal layer. Otherwise the heat-resistant metal layer may be formed using thin film technology such as flame melting spray, chemical plating, or evaporation. In this case, it is more preferable that a porous protective layer of alumina, spinel or the like is overlaid on the electrode layers 4, 5 using thick film technology.

Various heat-resistant ceramics may be used as the ceramic plate 7. Besides ceramics, metal plates having heat-resistant property may be used. The distance between the solid electrolyte plate 3 and the ceramic plate 7 (that is, the width of the gap 8) is preferably 0.01 –0.5 mm from the viewpoint of response property and measuring accuracy. The gap width may be varied if necessary so that it is widened slightly when relatively large current flows between the electrode layers 4, 5 or narrowed slightly when relatively small current flows.

Detection of the oxygen concentration in the exhaust gases of an automobile using the oxygen sensor 1 manufactured in the above-mentioned process is performed as hereinafter described.

First, in FIG. 2, a voltage of 15 V is applied to the heater 6 by the battery 11. When the heater 6 is not heated well and the oxygen pump element 50 is still at a low temperature, the atmospheric gas temperature does not sufficiently activate the oxygen sensor 1. Hence current does not flow through the solid electrolyte plate 3 between the electrode layers 4, 5. In this case, the heater 6 has a resistance of $2\Omega$ and each of the lead wires 14, 15 has a resistance of $0.5\Omega$. Consequently, a current of 5A flows through the heater 6 and the lead wires 14, 15.

As the temperature of the oxygen sensor 1 rises gradually, the oxygen sensor 1 is activated. Current begins to flow through the solid electrolyte 3, and thereby the oxygen concentration detecting action of the oxygen sensor 1 is started. As the temperature of the heater 6 rises, the resistance of the heater 6 increases from $2\Omega$ as above described to $10\Omega$. Also, the resistance of each of the lead wires 14, 15 increases from $0.5\Omega$ to about $0.7\Omega$. Since the resistance of the heater unit is divided in the ratio of about 7:3 by the junction 18, the voltage from the battery 11 is divided in the ratio of about 7:3. Consequently, the heater unit divided by the junction 18 is supplied with voltage in ratio of about 10.5 V:4.5 V. Thus the current flowing through the solid electrolyte plate 3 (which is a part of the oxygen pump element 50) becomes about 50 mA, because the oxygen pump element 50 has a resistance of about $100\Omega$ and the variable resistor has a resistance of $20\Omega$. The current 50 mA is sufficiently less than current 200 mA to break the oxygen pump. The voltage supplied then is about 5 V.

Figure 4:
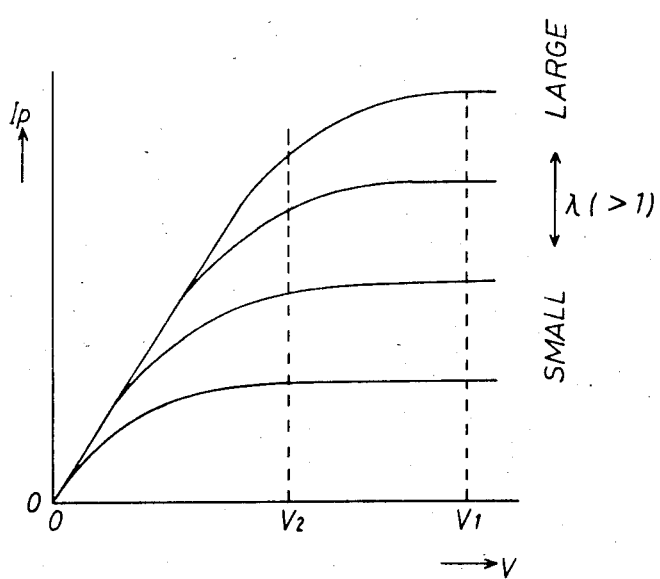
FIG. 4 is a graph illustrating the relation of the amount of current flowing through the oxygen sensor versus voltage in the first embodiment.

Next, the relation of the voltage and the current amount flowing between the electrode layers 4,5 has the relationship shown in FIG. 4 if the temperature is constant. In FIG. 4, the abscissa represents the voltage V between the two electrode layers 4,5, and the ordinate represents the amount of current $I_p$ flowing between the two electrodes 4, 5. If the oxygen concentration in the exhaust gases of the internal combustion engine (which is the measurement atmosphere of the oxygen sensor 1) is low, and hence if the air-fuel ratio λ is small (wherein ≧1), the current amount $I_p$ becomes constant at a relatively low voltage. On the contrary, if the oxygen concentration in the exhaust gases is high, and hence if λ is large, the current amount $I_p$ becomes constant at a relatively high voltage. Thus, if a suitable voltage, (e.g., the voltage $V_1$ shown in FIG. 4), is selected, the oxygen concentration in the exhaust gases can be calculated from the current amount $I_p$ flowing at that voltage.

The relationship shown in the graph of FIG. 4 is produced in that when voltage is applied to the electrode layer 4 at the plus side and to the electrode layer 5 at the minus side, the solid electrolyte plate 3 serves as an oxygen pump for pumping out oxygen and only oxygen in the gap 8. As the oxygen is exhausted through the solid electrode plate 3 towards the electrode layer 4, the oxygen concentration in the gap 8 is apt to decrease. Since the gap 8 is opened in three directions, the oxygen in the exhaust gases enters the gap 8 from the three directions by diffusion phenomenon. The diffusion of oxygen is limited by the width of the gap 8, and the pumping oxygen amount depends on the oxygen concentration in the exhaust gases if the temperature is approximately constant. Thus, since the oxygen concentration and hence oxygen amount exhausted by the solid electrolyte plate 3 is proportional to the amount of current flowing between the two electrode layers 4, 5, the current amount $I_p$ varies corresponding to the oxygen concentration at the suitable voltage $V_1$. Thus the oxygen concentration can be calculated by measuring $I_p$ as shown in the graph of FIG. 4.

According to this embodiment, the solid electrolyte plate 3 serving as the oxygen pump and the plate to constitute the gap for preventing the free flowing of the atmospheric gas to one electrode are provided close. Accordingly, the oxygen concentration in the atmospheric gases can be detected easily in the simple structure. Consequently, the yield rate becomes high during the manufacturing. Furthermore, since a wide space is not required to assemble the sensor, the assembling can be effected in a compact structure that is light in weight.

If a change-over switch is installed to change the current direction in the solid electrolyte plate, for example, when oxygen in exhaust gases of an internal combustion engine is measured, the air-fuel ratio can be measured precisely not only at lean mixture side but also at rich mixture side.

Figure 5:
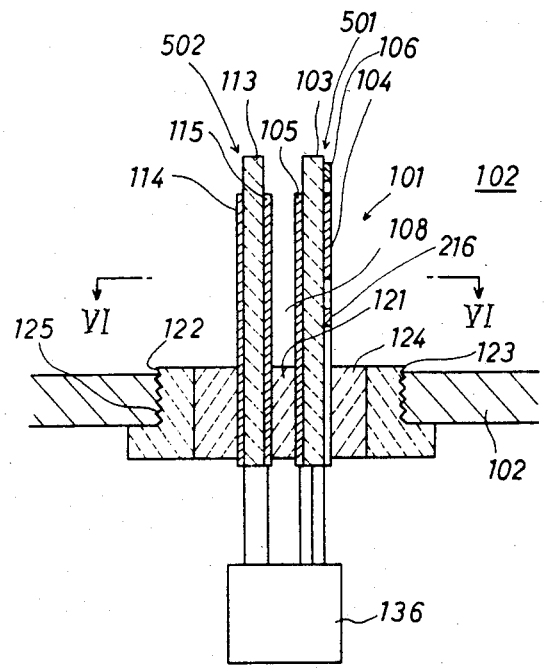
FIG. 5 is a diagram illustrating the constitution of an air-fuel ratio detecting device according to a second embodiment of the invention.
Figure 6:
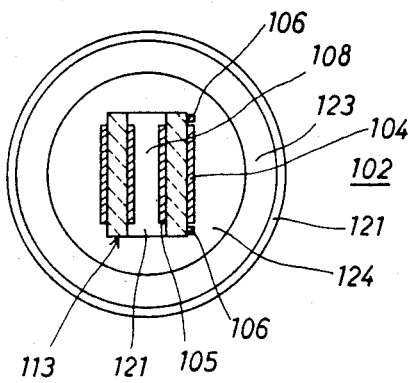
FIG. 6 is a sectional view taken along line VI—VI of FIG. 5.

A second embodiment of the invention as shown in FIG. 5 and FIG. 6 will now be described. The second embodiment is provided with an oxygen concentration cell element in place of the ceramic plate 7 in the first embodiment. In the figures, an oxygen sensor 101 is applied to an exhaust pipe 102 of an internal combustion engine. The oxygen sensor 101 has a similar structure to that of the oxygen pump element of the first embodiment as shown in FIG. 2. The oxygen sensor 101 is provided with a solid electrolyte oxygen pump element 501 comprising a solid electrolyte plate 103 (e.g. stabilized zirconia) in flat plate form with a thickness of about 0.5 mm and electrodes 104 and 105, each having a thickness of about 20μ. A heater 106 is formed respectively on the two side surfaces of the solid electrolyte plate 103 using thick film technology. An oxygen concentration cell element 502 comprises a solid electrolyte plate 113 in flat plate form in similar manner to the oxygen pump element. Electrodes 114 and 115 are formed on the two side surfaces of the solid electrolyte plate 113 in similar manner to the electrodes 104 and 105 using thick film technology. The solid electrolyte oxygen pump element 501 and the oxygen concentration cell element 502 are spaced by a gap 108 having a width of about 0.1 mm and are opposed to each other in the exhaust pipe 102 by fixing a foot portion of each element through a spacer 121 with heat-resistant and insulation property (A filler adhesive will do.). On the outside of the foot portion of the solid electrolyte oxygen pump element 501 and the oxygen concentration cell element 502 fixed mutually by the spacer 121 is installed a support bed 123 having a threaded portion 122 by an adhesive member 124 with heat-resistant and insulation property. The threaded portion 122 of the support bed 123 is screwed to a threaded portion 125 provided on the exhaust pipe 102 for installing a detecting plug member of the oxygen sensor 101. Thereby the oxygen sensor 101 is installed on the exhaust pipe 102. The electrodes 104, 105, the heater 106, and the electrodes 114 and 115 are connected to an electronic control unit 136.

Figure 7:
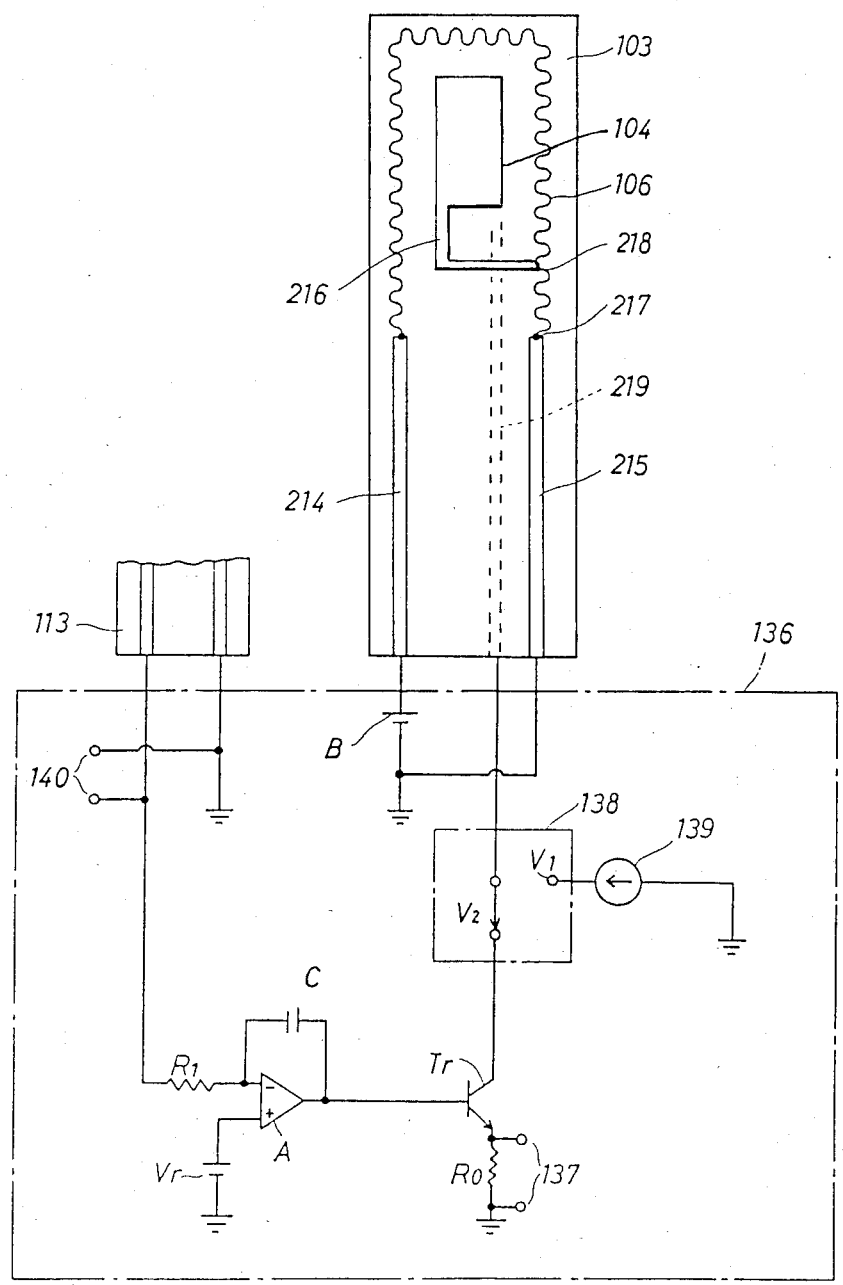
FIG. 7 is a plan view of an oxygen pump element.

FIG. 7 shows a plan view of the solid electrolyte oxygen pump element 501 of the oxygen sensor 101. In FIG. 7, the heater 106 is formed to the side of the electrode 104 at the edge portion outside the electrode 104 on the surface of the solid electrolyte plate 103. The heater 106 meanders in U-like form, and the solid electrolyte plate 103 is heated from the outer edge portion by energizing the heater 106. The two ends of the heater 106 are connected respectively to lead wires 214, 215 for the heater 106. One end of a lead wire 216 for the electrode 104 is connected to the heater 106 at a junction 218 slightly higher than a junction 217 of the heater 106 with the lead wire 215. The electrode 105 at the rear side of the electrode 104 is connected to a lead wire 219. The lead wires 216, 219 are made of material similar to that of the electrodes 104, 105—for example, platinum. The electrodes 104, 105, the heater 106, and the lead wires 214, 215, 216, and 219 are printed on the solid electrolyte plate 103 using thick film technology.

As previously mentioned, the numeral 136 designates an electronic control unit attached to the oxygen sensor 101. The electronic control unit 136 causes an electromotive force e generated between the electrode 114 and the electrode 115 of the oxygen concentration cell element 502 to be applied to the inversion input terminal of an operation amplifier A through a resistor $R_1$. A reference voltage $V_r$ is applied to the non-inversion input terminal of the operation amplifier A. Thus, the output of the operation amplifier A is proportional to the difference between the reference voltage $V_r$ and the electromotive force e. That output drives a transistor $T_r$ so as to control the pump current flowing between the electrodes 104, 105 of the solid electrolyte oxygen pump element 501. That is, the pump current $I_p$ necessary to hold the electromotive force e to the definite value $V_r$ is supplied. A resistor $R_o$ is installed so that the output signal supplied from a DC power source B corresponding to the pump current $I_p$ is obtained at an output terminal 137. The symbol C designates a capacitor. The numeral 138 designates a change-over switch installed at one end of the input/output terminals of the solid electrolyte oxygen pump element 501. In this embodiment, the change-over switch 138 is set either to $V_1$ for connection to a constant-current source 139 so that solid electrolyte oxygen pump element 501 pumps oxygen from the exhaust gases within the exhaust pipe 102 into the gap 108 or to $V_2$ for connection to the control circuit side so as to obtain an output signal corresponding to the pump current Ip when the solid electrolyte oxygen pump element 501 pumps oxygen from the gap 108 into the exhaust pipe 102 so that output of the oxygen concentration cell element is held constant. An output terminal 140 is installed to detect the electromotive force e.

Figure 8:
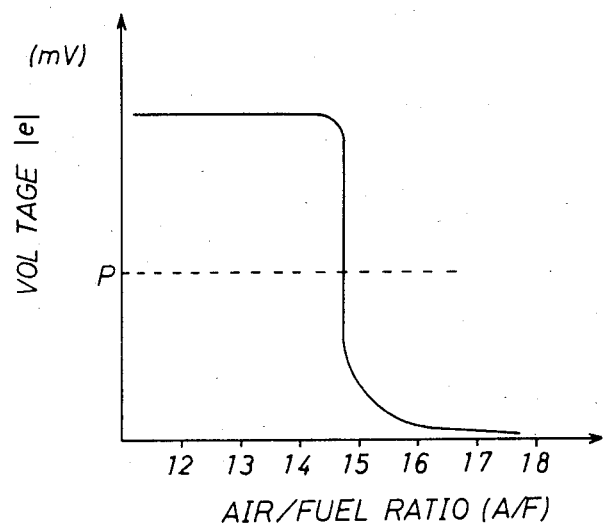
FIG. 8 is a characteristic diagram illustrating variation of electromotive force e of an oxygen concentration cell element with respect to the air-fuel ratio when the pumping current $I_p$ of the oxygen pump element is constant.
Figure 9:
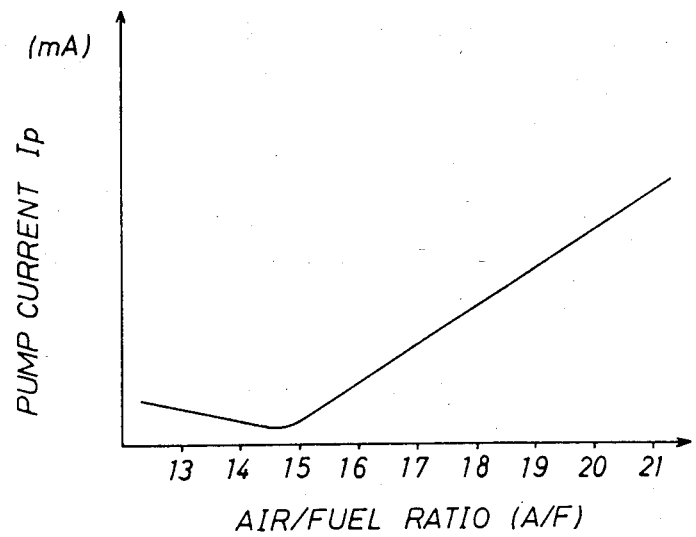
FIG. 9 is a characteristic diagram illustrating variation of pumping current $I_p$ of the oxygen pump element with respect to the air-fuel ratio when the pumping electromotive force e of the oxygen concentration cell element is constant.

FIG. 8 and FIG. 9 are characteristic diagrams of the second embodiment shown in FIG. 5 and FIG. 6.

FIG. 8 shows the electromotive force e when the oxygen pump element 501 pumps oxygen from exhaust gases of the exhaust pipe 102 into the gap 108. FIG. 8 shows the variation of the electromotive force e (e<0) when the constant-current source 139 is held to −50 mA and the air-fuel ratio (A/F) is varied. The electromotive force e increases corresponding to increase of the air-fuel ratio from about 12, rapidly decreases at the theoretical air-fuel ratio 14.7, and is scarcely generated in the range of the theoretical air-fuel ratio beyond 14.7 (lean fuel range).

FIG. 9 shows variation of the pump current $I_p$ when the reference voltage Vr is held at 20 mV for example. If the electromotive force e (e>0) is made 20 mV, the pump current $I_p$ ($I_p$>0) decreases corresponding to increase of the air-fuel ratio in the range of the ratio less than the theoretical air-fuel ratio 14.7 (rich fuel range) and increases corresponding to increase of the air-fuel ratio in the range of the ratio beyond the theoretical air-fuel ratio 14.7 (lean fuel range). The second embodiment utilizes characteristics as shown in FIG. 8 and FIG. 9.

For example, when the change-over switch 138 is set at $V_1$, characteristics of FIG. 8 can be obtained at an output terminal 140 to detect the electromotive force e. Utilizing those characteristics, an arbitrary reference point P is set at medium range between the maximum electromotive force and the minimum electromotive force, and detection is effected when the voltage is greater than that of point P (rich fuel range) and when the voltage is less than that of point P (lean fuel range). When the engine is operated in the rich fuel range (air-fuel ratio being 13 or more and less than 14.7 in the second embodiment), the electromotive force e of the oxygen concentration cell element 10 is larger than that at point P, and the value in the rich fuel range can be measured by detecting output signals of the electromotive force e at this time. When the engine is operated in the lean fuel range, the electromotive force e of the oxygen concentration cell element is smaller than that of point P, and the changeover switch 138 is set at $V_2$ from that information. Thereby, the characteristics of FIG. 9 can be obtained at the output terminal 137 to detect the pump current $I_p$, and the values in the lean fuel range can be measured by detecting output signals corresponding to the pump current $I_p$ of the solid electrolyte oxygen pump element 501. When the engine is operated at the theoretical air-fuel ratio 14.7, the change-over switch 138 is set at $V_1$, and the measurement is performed by rapid variation of the electromotive force e of the oxygen concentration cell element 502.

According to the above-mentioned constitution, an oxygen sensor is obtained in which the value of the air-fuel ratio of the engine can be accurately measured even at wide variations of rich fuel range and lean fuel range. If objective air-fuel ratio is set utilizing this constitution, the air-fuel ratio in the existing state can be detected by the air-fuel ratio detecting plug attached to the exhaust pipe 102, and a desired air-fuel ratio can be continuously controlled according to feedback of the detected ratio.

Figure 10:
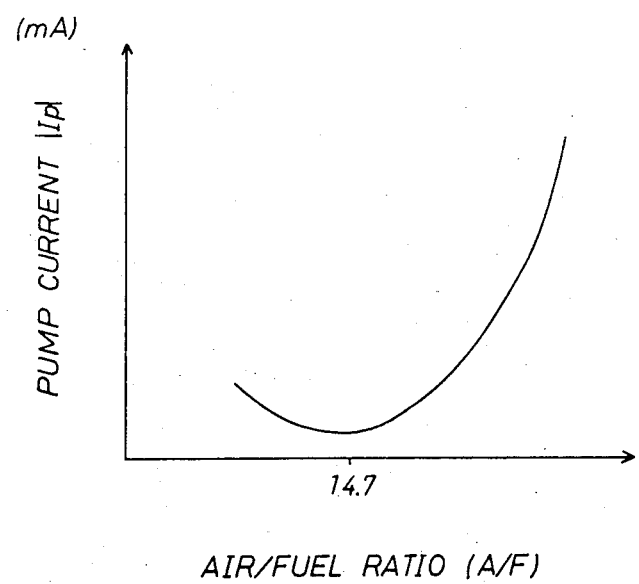
FIG. 10 is a characteristic diagram illustrating variation of pumping current $I_p$ of the oxygen pump element with respect to the air-fuel ratio when the pumping electromotive force e of the oxygen concentration cell element is constant.

In the second embodiment, the pump current $I_p$ used as control signal in the lean fuel range flows in such direction that oxygen is pumped from a narrow gap a into the exhaust pipe 102 ($I_p$>0) or in such direction that oxygen is pumped from the exhaust gases within the exhaust pipe 102 into the narrow gap a ($I_p$<0). FIG. 10 shows the variation of the pump current $I_p$ when the output of the electromotive force e (e<0) is constant. Since the air-fuel ratio (A/F) and the pump current $I_p$ vary corresponding to each other, the characteristics also can be utilized.

Figure 11:
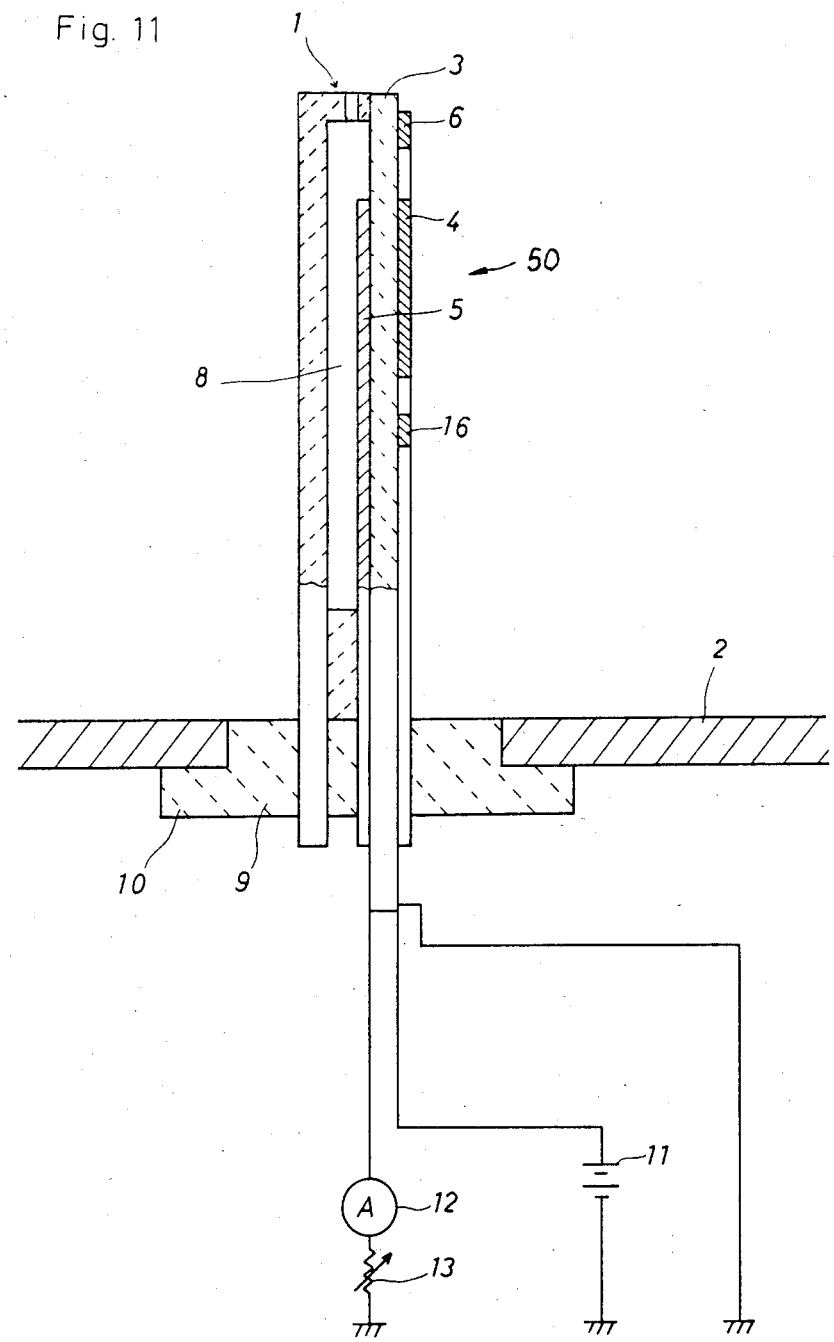
FIG. 11 is a diagram illustrating the constitution of an air-fuel ratio detecting device according to a third embodiment of the invention.

In a third embodiment (shown in FIG. 11), a narrow gap is constituted between the oxygen pump element and the ceramic plate or the oxygen concentration cell element in opposition to the oxygen pump element, and a portion at the open end edge side of the narrow gap is made as a diffusion resistance supplying means. However, in addition to the diffusion limiting system according to such flat hole or passage, a system where an adaptor to constitute a closed chamber in co-operation with the oxygen pump element is provided with fine holes, and the oxygen diffusion resistance is supplied by the fine holes. Thus a system of supplying the diffusion resistance according to a porous member of the like may be widely adapted. Although one electrode of the oxygen pump element is exposed directly to ambient gases to be measured in the embodiment, the electrode may be exposed to a reference oxygen source, for example, a chamber to introduce air.

In the oxygen sensor of the invention, since the heater unit 6, 106 is connected to the lead wire 16, 216, and the power source may be used commonly for the heater unit 6, 106 and the oxygen pump element 50, 501, the number of wires to connect the sensor probe to the power source circuit or the control circuit is reduced. Furthermore, since a special circuit is not required to prevent breakage of the oxygen pump element, the power source circuit or the control circuit may be simplified.

Common use of the power source facilitates the temperature control and the current control of the oxygen sensor 1, 101.

Thermal efficiency can be improved by applying voltage to the heater.

Since voltage applied to the solid electrolyte as the oxygen pump can be previously adjusted by changing the position of the junction 18, 218 suitably, freedom in the design can be improved, and excessive current can be prevented from flowing in the solid electrolyte plate. Consequently, the life of the oxygen sensor 1, 101 can be lengthened.

Since heating by the heater and pumping of oxygen are performed simultaneously on the same solid electrolyte plate 3, 103 using the same power source, the number of lead wires for the heater 6, 106 may be reduced. Since the lead wire 16, 216 is connected to the heater 6, 106, the use amount of the lead wire 16, 216 of platinum for the power source 4, 104 may be decreased, and the cost may be reduced also in this aspect.

It is clear that many different modifications of the invention may be made without departing from the spirit and scope thereof.

What is claimed is:

1. An oxygen sensor comprising:

(a) a solid electrolyte plate (3, 103) with oxygen ion conductive property, said solid electrolyte plate (3, 103) having a front surface and a rear surface;

(b) a first electrode (4, 104) and a second electrode (5, 105) formed respectively on the front and the rear surfaces of said solid electrolyte plate (3, 103);

(c) a heater unit (6, 106) formed on the front surface of said solid electrolyte plate (3, 103), said heater unit (6, 106) having a first end and a second end;

(d) a lead wire (16, 216) electrically connecting said first electrode (4, 104) to said heater unit (6, 106) intermediate the ends of said heater unit (6, 106);

(e) an external power source (11, 113) for supplying voltage between said first electrode (4, 104) and said second electrode (5, 105) through said heater unit (6, 106) and said lead wire (16, 216) so that a controlled pumping current flows between said first electrode (4, 104) and said second electrode (5, 105); and (f) an oxygen diffusion limiting means (8, 108) in fluid communication with said second electrode (5, 105), whereby oxygen from ambient gases to be measured is pumped from said oxygen diffusion limiting means (8, 108) through said solid electrolyte plate (3, 103).

2. An oxygen sensor as set forth in claim 1, wherein said oxygen diffusion limiting means (8, 108) comprises:
   (a) a ceramic plate (7) functioning as an oxygen gas shielding body and arranged opposite said second electrode (5) and
   (b) a gap (8) between said ceramic plate (7) and said solid electrolyte plate (3).

3. An oxygen sensor as set forth in claim 2, wherein the first and second electrodes (4, 5) include a heat-resistant metal layer formed in a process wherein:
   (a) a powder, the main constituent of which is selected from the group consisting of Pt, Ru, Pd, Rh, Ir, Au, and Ag, is converted into a paste state;
   (b) the paste is printed on said solid electrolyte plate (3) using thick film technology; and
   (c) the paste is then sintered.

4. An oxygen sensor as set forth in claim 2, wherein:
   (a) said gap (8) is previously set so that the gap width is proportional to the amount of said pumping current, and
   (b) said heater unit (6) meanders.

5. An oxygen sensor as set forth in claim 2, wherein:
   (a) said gap (8) is formed as a closed chamber by an adaptor, and
   (b) oxygen in ambient gases flows in said closed chamber through fine holes provided in said adaptor.

6. An oxygen sensor as set forth in claim 1, wherein:
   (a) a lead wire (14) is connected to the first end of said heater unit (6) and to the positive electrode of said external power source (11);
   (b) the negative electrode of said external power source (11) is grounded;
   (c) a lead wire (19) is connected to said second electrode (5) and to an ammeter (12) and a variable resistor (13) which is grounded; and
   (d) a lead wire (15) connected to the second end of said heater unit (6) is grounded.

7. An oxygen sensor as set forth in claim 1, wherein said solid electrolyte plate (3) is:
   (a) made of a sintered body of solid electrolyte including zirconia as the main constituent and
   (b) formed into a rectangular flat plate.

8. An oxygen sensor as set forth in claim 1, wherein:
   (a) an oxygen concentration cell element (502) is arranged opposite said second electrode (105);
   (b) said oxygen diffusion limiting means (8,108) comprises a gap (108) formed between said second electrode (105) and said oxygen concentration cell element (502); and
   (c) said oxygen concentration cell element (502) comprises a third electrode (114) and a fourth electrode (115) on front and rear surfaces respectively of a second solid electrolyte plate (113).

9. An oxygen sensor as set forth in claim 8, wherein:
   (a) electromotive force e generated between said first electrode (114) and said second electrode (115) of said oxygen concentration cell element (502) is entered through a resistance into the inversion input terminal of an operational amplifier (A);
   (b) voltage proportional to the difference between a reference voltage Vr entered into the non-inversion input terminal of said operational amplifier (A) and said electromotive force e is output;
   (c) said operational amplifier (A) connected to said resistance acts so that said electromotive force e approaches said reference voltage Vr;
   (d) an external power source (139) is provided so that voltage is applied to said first and second electrodes (104, 105); and
   (e) oxygen is pumped from ambient gases to be measured through said first and second electrodes (104, 105) into said gap (108).

10. An oxygen sensor as set forth in claim 9, wherein a switch ($V_1$, $V_2$) is connected to a lead wire (219) and selectively connected:
    (a) at the $V_2$ side thereof to the output side of said operational amplifier (A) through the collector side of a transistor (Tr) so that oxygen from ambient gases to be measured is pumped through said gap (108) with oxygen diffusion limiting property to the side of said first electrode (104) and so that the pumping current flowing between said first and second electrodes (104, 105) depending on oxygen concentration in the ambient gases to be measured is detected or
    (b) at the $V_1$ side thereof to said external power source (139) so that oxygen is pumped into said gap (108), whereby:
    (c) if the switch is connected to the $V_1$ side and the decision from comparison of said electromotive force e with a prescribed voltage P is that said electromotive force e is greater than the prescribed voltage P, oxygen in ambient gases to be measured is discriminated to be rich and said electromotive force e is measured, and,
    (d) if the decision from comparison of said electromotive force e with the prescribed voltage P is that the electromotive force e is smaller than the prescribed voltage P, oxygen in ambient gases to be measured is discriminated to be lean and the switch is changed from the $V_1$ side to the $V_2$ side and said pumping current is measured.

* * * * *